(12) United States Patent
Dong et al.

(10) Patent No.: US 9,399,616 B2
(45) Date of Patent: Jul. 26, 2016

(54) PROCESS FOR THE MANUFACTURE OF 4-AMINOBENZOAMIDINE DIHYDROCHLORIDE

(71) Applicants: Weitong Dong, Shanghai (CN); Christian Wolfgang Hemp, Shanghai (CN); Xiangle Jin, Shanghai (CN); Jun Lu, Shanghai (CN); Ulrich Scholz, Biberach (DE); Shengmin Su, Shanghai (CN); Wei Xu, Shanghai (CN); Jinsong Yang, Ingelheim am Rhein (DE)

(72) Inventors: Weitong Dong, Shanghai (CN); Christian Wolfgang Hemp, Shanghai (CN); Xiangle Jin, Shanghai (CN); Jun Lu, Shanghai (CN); Ulrich Scholz, Biberach (DE); Shengmin Su, Shanghai (CN); Wei Xu, Shanghai (CN); Jinsong Yang, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 185 days.

(21) Appl. No.: 14/055,054

(22) Filed: Oct. 16, 2013

(65) Prior Publication Data

US 2014/0114089 A1 Apr. 24, 2014

(30) Foreign Application Priority Data

Oct. 22, 2012 (CN) .................. PCT/CN2012/083317

(51) Int. Cl.
| | | |
|---|---|---|
| *C07C 257/08* | (2006.01) | |
| *C07C 257/18* | (2006.01) | |
| *C07C 249/02* | (2006.01) | |

(52) U.S. Cl.
CPC ............. *C07C 249/02* (2013.01); *C07C 257/08* (2013.01); *C07C 257/18* (2013.01)

(58) Field of Classification Search
None
See application file for complete search history.

(56) References Cited

U.S. PATENT DOCUMENTS

2011/0275824 A1 11/2011 Gnad et al.
2013/0158270 A1 6/2013 Gnad et al.

FOREIGN PATENT DOCUMENTS

WO 2011061080 A1 5/2011

OTHER PUBLICATIONS

International Search Report, PCT/EP2013/071884, mailed Jan. 20, 2014.
Yun-Ji, Journal of Materials Chemistry, "Syntheses of novel 1,3-diazaazulene derivatives and their nonlinear optical characterization", vol. 17, 2007, p. 2101-2106.
Yun-Ji, Journal of Materials Chemistry, Supporting Information, 2007, p. 1-9.
Xiao-Hua, Journal of Polymer Science Part B: Polymer Physics, "Chiral Crystal of a Czy-Symmetric 1,3-Diazaazulene Derivative Shownig Efficient Optical Second Harmonic Generation", vol. 49, No. 9, 2011, p. 649-656.
Stolic, Croatia Chemica Acta, "Synthesis, DNA Interactions and Anticancer Evaluation of Novel Diamidine Derivatives of 3,4-Ethylenedioxythiophene", vol. 85, No. 4, 2012, p. 457-467.

*Primary Examiner* — Sudhakar Katakam
*Assistant Examiner* — Jennifer C Sawyer
(74) *Attorney, Agent, or Firm* — Michael P. Morris; Timothy X. Witkowski

(57) ABSTRACT

The present invention relates to a process for the preparation of 4-aminobenzoamidine (4-AMBA) salts of general formula (I)

preferably the salts thereof with hydrochloric or hydrobromic acid, particularly preferred the dichloride salt.

12 Claims, No Drawings

PROCESS FOR THE MANUFACTURE OF 4-AMINOBENZOAMIDINE DIHYDROCHLORIDE

The present invention relates to a process for the preparation of 4-aminobenzoamidine (4-AMBA) salts of general formula (I)

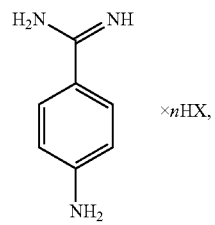

preferably the salts thereof with hydrochloric or hydrobromic acid, particularly preferred the dichloride salt.

BACKGROUND TO THE INVENTION

A compound of formula (I) is a key intermediate for Dabigatran etexilate, which is known as an orally active prodrug for the reduction of stroke and systemic embolism. It was first disclosed in WO 98/37075. Processes for the manufacture of dabigatran etexilate are also known from WO 2006/000353 or described by Hauel et al. (J. Med. Chem, 2002, 45. 1757 ff).

Another process for the manufacture of Dabigatran is described by Zerban et al. (WO2006000353), However this process requires the use of an ecologically unfavorable dehydration agent.

Therefore a new process was developed by Gnad et al., as described in WO 2011/061080, circumventing the use of this dehydration agent. This process requires the use of the herein described intermediate 4-AMBA.

One of the current manufacturing routes of 4-aminobenzoamidine starts from 4-aminobenzonitrile via the 4-amino-N-hydroxybenzamidine intermediate (IV) (see Scheme 2).

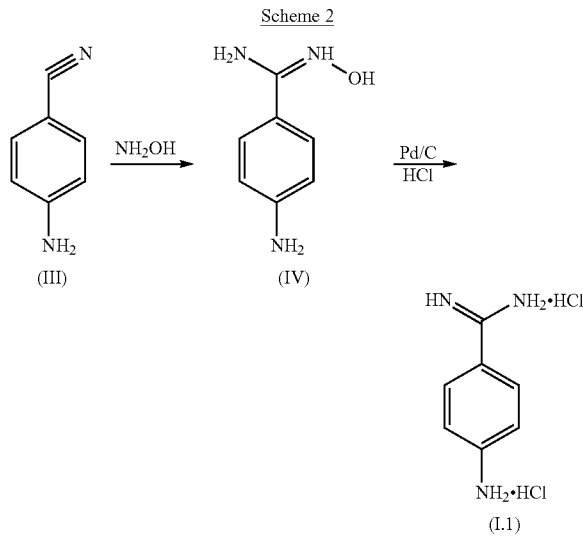

This process requires usage of the expensive catalyst Pd/C and the hazardous reagent $NH_2OH$, which is explosive and potentially mutagenic (Zerban Georg et al WO 2007/071743). It is well known that imidates can be prepared through the so called Pinner reaction by condensing a nitrile and an alcohol in the presence of anhydrous hydrogen chloride, hydrogen bromide or a base (Journal of Polymer Science, Part B: Polymer Physics (2011), 49, 649).

The prior art already describes a process for preparing Intermediate (II) (R=ethyl) Ethyl 4-aminobenzimidine and subsequent transformation to 4-AMBA (I) through Pinner reaction. However this process suffers from serious drawbacks for application on commercial scale. Thus described by Xiao-Hua Ma et al in Journal of Polymer Science, Part B: Polymer Physics (2011), 49, 649, the reaction was conducted at elevated temperatures on small scale and with reaction times of 20 h and bubbling of Hydrogen Chloride through the solution. On larger scale however, the high temperature and the long reaction time lead to uncontrollable decay of the reaction intermediates resulting in low yields and unsafe conduction of the reaction. Additionally the chosen setup is suitable for lab scale only and the used absolute ethanol renders the synthesis uneconomical. Use of cheaper alcohol solvents has not been described, most probably due to bad solubility of the intermediates in those solvents.

The problem underlying the present invention is to provide a process which circumvents the use of toxic, explosive or very expensive ingredients. Preferably the aim of the present invention is to overcome the drawbacks linked to the present process and to deliver an efficient, scalable, ecological feasible, robust and safe process for the manufacture of 4-AMBA (I) starting from 4-ABN (III), therefore requiring shorter reaction times, lower temperatures and circumventing the use of expensive reagents or solvents.

DESCRIPTION OF THE INVENTION

The present invention solves the above-mentioned problems, particularly the problems related to the current synthetic route (see Scheme 2) and also the problems mentioned in the above cited prior art concerning the Pinner process in ethanol, by the method of synthesis described hereinafter.

The invention thus relates to a process for the preparation of a compound of formula (I),

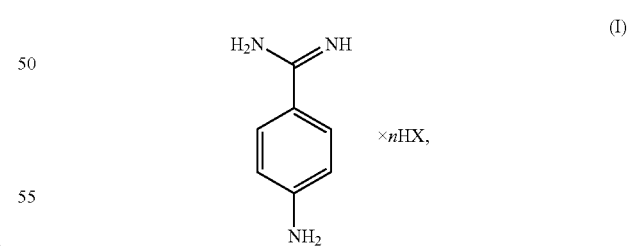

wherein
n denotes 1 or 2, preferably 2,
X denotes Cl or Br, preferably Cl,
wherein the process comprises reaction step (B),
wherein
  in step (B):
    the imidate salt (II) is treated with an alcoholic solution, e.g methanol, ethanol, propanol or butanol respectively, of ammonia,

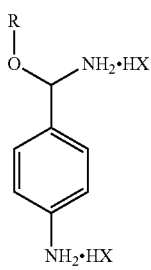

(II)

wherein
R denotes methyl, ethyl, propyl or butyl, preferably methyl or ethyl, particularly preferred methyl,
X denotes Cl or Br, preferably Cl.

Preferred is a process for the preparation of a compound of formula (I),
wherein the process comprises reaction steps (A) and (B), wherein
in step (A):
4-aminobenzonitril (III) is treated with HX, preferably hydrogen chloride or hydrogen bromide, particularly preferred hydrogen chloride, in a pure or mixed alcoholic solvent, e.g. a mixture of one alcohol with another less polar solvent such as toluene, heptane, chloroform or dichloromethane, at a pressure of about 0 to 10 atm,

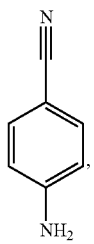

(III)

to form an imidate salt (II);

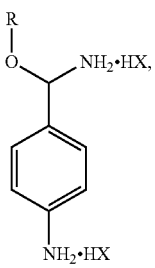

(II)

preferably an imidate salt (II.1)

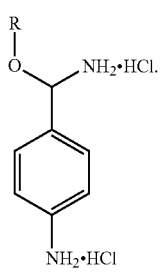

(II.1)

with the provisio that if R denotes ethyl, the reaction pressure is between 2 to 6 atm.

Also preferred is a process for the preparation of a compound of formula (I),

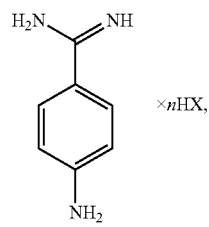

(I)

wherein
n denotes 1 or 2, preferably 2,
X denotes Cl or Br, preferably Cl,
wherein the process comprises reaction steps (A), (B) and (C),
wherein
in step (A):
4-aminobenzonitril (III) is treated with HX, preferably hydrogen chloride or hydrogen bromide, in a pure or mixed alcoholic solvent at a pressure of about 0 to 10 atm,

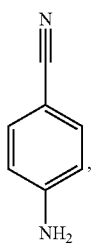

(III)

to form an imidate salt (II);

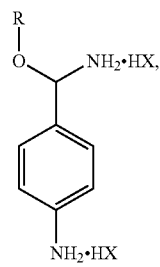

(II)

with the provisio that if R denotes ethyl, the reaction pressure is between 2 to 6 atm.
in step (B):
the imidate salt (II) is treated with an alcoholic solution of ammonia,
wherein
R denotes methyl, ethyl, propyl or butyl,
X denotes Cl or Br
and
in step (C):
compound (I) is precipitated by acidification with aqueous HX, preferably hydrogen chloride,
while the steps (A), (B) and (C) take place successively in the order specified.

Another embodiment of the invention is a process for the preparation of a compound of formula (II), wherein the process comprises reaction step (A), wherein
in step (A):
4-aminobenzonitril (III) is treated with HX in a pure or mixed alcoholic solvent at a pressure of about 0 to 10 atm,

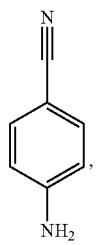
(III)

to form an imidate salt (II);

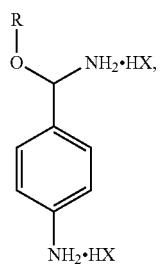
(II)

wherein
R denotes methyl, ethyl, propyl or butyl, preferably methyl, and
X denotes Cl or Br, preferably Cl,
with the provisio that if R denotes ethyl, the reaction pressure is between 2 to 6 atm.

Also preferred is a process for the preparation of a compound of formula (I) or (II), wherein the alcoholic solvent utilized is ethanol or methanol.

Also preferred is a process for the preparation of a compound of formula (I) or (II), wherein the alcoholic solvent utilized is methanol.

Also preferred is a process wherein the alcoholic solvent in step (A), (B) and (C) is the same.

Also preferred is a process wherein the concentration of HCl or HBr in step (A) or step (B) is from 5% to 30% (weight %) in alcohol.

Also preferred is a process wherein the molar ratio of HCl or HBr to compound (III) is from 2:1 to 20:1, preferably from 5:1 to 10:1.

Also preferred is a process wherein the reaction according to step (A) is conducted at a temperature from −10° C. to 80° C., preferably from 0° C. to 60° C., particularly preferred from 30° C. to 50° C.

Also preferred is a process wherein the amination step (B) is running at the temperature from 20° C. to 80° C.

Also preferred is a process wherein the reaction is running in NH$_3$ solved in an alcohol solution with a concentration of NH$_3$ from 5% to 30% (weight %).

Also preferred is a process wherein the molar ratio of NH$_3$ to imino ether (II) is 2:1 to 10:1.

A further embodiment of the present invention is the use of compound (I) as prepared by the process described above for the production of dabigatran etexilate.

A further embodiment of the present invention is a compound of formula (II), wherein R denotes methyl and X denotes Cl.

Especially the present invention relates to a novel process for the preparation of the 4-aminobenzoamidine (4-AMBA) dihydrochloride of formula (I.1) from 4-Aminobenzonitrile (4-ABN) of formula (III) via intermediacy of imidate (II.1) according to the following scheme 1, without the necessity to use toxic, explosive or very expensive reagents:

Scheme 1

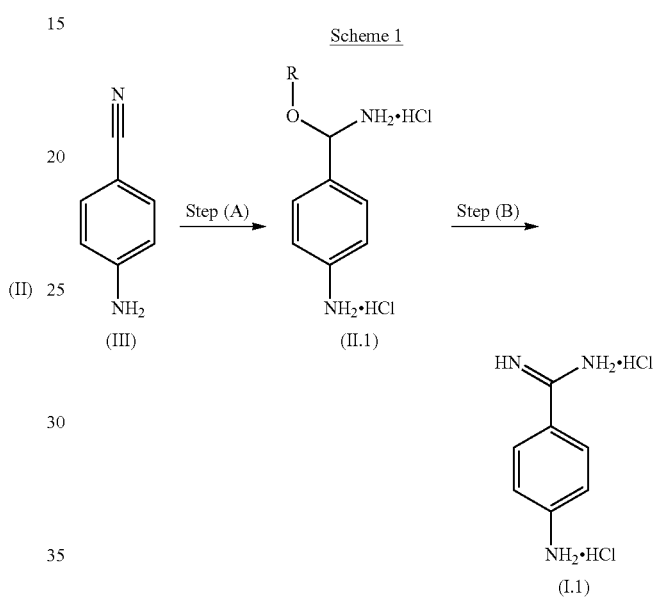

The substituent R denotes Me, Et, Pr or Bu, preferably Me or Et, particularly preferred Me.

Compound of formula (I) is produced by Pinner reaction and amination according to the reaction scheme 1.

As the reagent in process step (A), a solution of HCl (gas) in alcohol is used. Usually, the concentration of the HCl is 5% to 30% (weight %) in alcohol. Preferably the concentration is 15%-20% (weight %). Usually, the molar ratio of HCl to 4-ABN (III) is 2 to 20. Preferably the molar ratio of HCl to 4-ABN (III) is 5 to 15.

Usually the alcohol used as a reagent in step (A) is methanol, ethanol, propanol or butanol, preferably methanol or ethanol, particularly preferred methanol.

Usually the alcoholic solvent used in step (A) or (B) is methanol, ethanol, propanol or butanol, preferably methanol or ethanol, particularly preferred methanol.

Usually the mixed alcoholic solvent used in step (A) or (B) is a mixture of methanol/ethanol, methanol/ethanol with toluene, methanol/ethanol with dichloromethane, methanol/ethanol with chloroform or methanol/ethanol with heptane.

By the term "alcohol" absolute alcohol or alcohol containing up to 0.1% (weight %) water is meant within the scope of the invention. Accordingly by the terms "methanol", "ethanol", "propanol" and "butanol" absolute methanol, absolute ethanol, absolute n-propanol and absolute n-butanol, optionally containing up to 1% (weight %) water is meant within the scope of the invention.

Step (A) is carried out at a pressure of 0 to 10 atm. The preferred reaction pressure is between 2 to 6 atm.

Step (A) is performed at a temperature of about −10 to 110° C. The preferred reaction temperature is about 30 to 50° C.

Particularly preferred step (A) is carried out in a solution of HCl (gas) in ethanol at a pressure of 2 to 6 atm and a reaction temperature of 30 to 50° C.

Also particularly preferred step (A) is carried out in a solution of HCl (gas) in methanol at a pressure of 2 to 6 atm and a reaction temperature of 30 to 50° C.

As a reagent for the amination step (B), a solution of $NH_3$ in alcohol is used. Usually, the concentration of the $NH_3$ in alcohol is about 5% to 30% (weight %), preferably 10% to 20% (weight %).

Usually in step (B) the molar ratio of $NH_3$ to imino ether (II) is from 2:1 to 20:1; preferably the molar ratio of $NH_3$ to imino ether (II) is from 3:1 to 6:1, particularly preferred from 4:1 to 5:1

The amination (step B) is conducted at a temperature from 18 to 110° C. The preferred reaction temperature is from 20 to 80° C., preferably from 40 to 60° C.

In order to prevent the accumulation of inorganic impurities in the 4-AMBA dihydrochloride (I.1), during the workup of the amination step B, calciumhydroxide may be added to remove ammoniumchloride. Alternatively this step can be replaced by a hot filtration during workup to remove ammoniumchloride As an advantage of the present invention, the Pinner reaction run in a closed system utilizing pressure is significantly faster, potentially due to the increase of HCl concentration in the reaction system, even at much lower reaction temperatures and in solvents that are not well dissolving the product. Side reactions such as hydrolysis of imino ether are minimized and thus the reaction selectivity and yield are increased compared to the process described in the prior art. The yield of the product and its purity are very high. Therefore the efforts needed for purification are significantly reduced. At the same time the expected side reaction of the alcoholic solvent with e.g. the anhydrous hydrogen chloride to form the corresponding chlorides can be well controlled at the low temperature and in the absence of Lewis acid catalysts.

Compared to the existing route of synthesis utilizing hydroxylamine an additional surprising effect can be observed that no side products are formed which in the downstream process of the Dabigatran synthesis may form colored intermediates, requiring additional purifying steps. This is an advantage with respect to product quality. The reagents (HCl (gas), MeOH/ethanol, $NH_3$) are easily available in good quality and are inexpensive.

Another advantage of the process according to the invention is that it can be conducted in only one solvent for the whole process. The solvents (alcohols) used in the reaction can but do not have to be recycled easily after distillation and drying, rendering the process both more economical and ecological.

The following examples serve to illustrate the process for preparing the compound of formula (I) according to Scheme 1 carried out by way of example. These examples are to be taken as an illustration of the invention without restricting the latter to its subject-matter.

EXAMPLES

Example 1

Step A Pinner Reaction 515 mL (8.5 v/w of 4-ABN) ethanol and 60.8 g (0.514 mol, 1.0 eq) 4-ABN are charged into a 1000 mL flask under $N_2$, obtained a solution. Then cooled to −10° C., 240.0 g (6.58 mol, 12.8 eq) HCl gas is bubbled into the reaction solution (dried through conc. $H_2SO_4$) while keeping the temperature below 20° C. Heated up to 35~40° C. the reaction is monitored by HPLC and checked every 4 h. The reaction is finished in about 16 h. The reaction mixture is cooled down to room temperature (rt=20 to 22° C.) and stirred 1 h. The suspension is filtered to obtain 194.8 g of wet product (Ethyl 4-aminobenzimidine salt) as solid 92.85% HPLC purity.

Mass spectrum (ESI$^+$): m+1−2HCl/z=165;

$^1$H NMR: $\delta_H$ 1.36-1.43 (3H, triple, 7-C); 4.51-4.57 (2H, tetra, 6-C); 6.76-6.80 (2H, d, 3-C); 7.90-7.99 (2H, d, 2-C).

$^{13}$C NMR: $\delta_C$13.6 (7-C); 68.4 (6-C); 111.2 (1-C); 114.0 (3-C); 123.1 (2-C); 133.5 (4-C); 169.5 (5-C).

Step B and C Amination and Precipitation 45 mL (3 v/w of 4-ABN) ethanol and 48.7 g wet intermediate (Ethyl 4-aminobenzimidine salt) ($C_9H_{12}N_2O.2HCl$, from 0.129 mol 4-ABN) are charged into a 250 mL flask under $N_2$ at rt. 103.0 g (10.6% in ethanol, 0.64 mol, 5.0 eq) ammonia ethanol solution is added drop wise into the flask while keeping the temperature below 35° C. After addition the reaction mixture is heated up to 35~40° C. and stirred for 2 h. 5.3 g (0.072 mol, 0.55 eq) $Ca(OH)_2$ are charged into the flask, then heated up to 45~50° C. and stirred at this temperature 0.5 h. Hot filtration is used to remove some inorganic insoluble impurities to obtained 160.0 g of filtrate. Excess of $NH_3$ in the filtrate is removed by distillation under vacuum. After distillation, the resulting residue is diluted by adding fresh ethanol and then heated up to 60~70° C. 30.6 g (0.31 mol, 2.4 eq) conc. HCl aq. is added dropwise into the flask and stirring continued at 60~70° C. for 0.5 h, then cooled down to 0~5° C. slowly, stirring continued for 1 h. The suspension is then filtered and washed with ethanol to obtain 40.8 g wet product as solid, which is dried at 55° C. under a vacuum for 6 h to obtain 22.6 g product as solid. Isolated yield 84% with 98.5% HPLC purity.

Mass spectrum (ESI$^+$): m+1−2HCl/z=136

Example 2

Step A Pinner Reaction 82 mL (6.8 v/w of 4-ABN) methanol and 12.0 g (0.102 mol, 1.0 eq) 4-ABN are charged into a 250 mL flask under $N_2$ to give a solution. The mixture is then cooled to −10° C., 37.0 g (1.02 mol, 10.0 eq) HCl gas is bubbled into the reaction solution (dried through conc. $H_2SO_4$) while keeping the temperature below 20° C. After bubbling the HCl gas, the reaction mixture is set to 25~30° C. and allowed to stir for 34 h. Then the mixture is filtered to give 25.3 g of wet product as solid. This product is used in next step without further treatment.

Mass spectrum (ESI$^+$): m+1−2HCl/z=151;

$^1$H NMR: $\delta_H$ 4.17-4.19 (3H, s, 6-C); 6.70-6.74 (2H, d, 3-C); 7.88-7.92 (2H, d, 2-C).

$^{13}$C NMR: $\delta_C$ 58.9 (6-C); 113.3 (1-C); 122.6 (3-C); 128.9 (2-C); 131.4 (4-C); 166.9 (5-C).

Step B and C Amination 35 mL (3 v/w of 4-ABN) ethanol and 25.3 g wet intermediate ($C_9H_{12}N_2O.2HCl$, from 0.102 mol 4-ABN) are charged into a 250 mL flask under $N_2$ at rt. 77.2 g (11.2% in ethanol, 0.508 mol, 5.0 eq) ammonia ethanol solution is added drop wise into the flask while keeping the temperature below 35° C. After complete addition, the mixture is heated up to 35~40° C. and allowed to stir for 2 h. 4.14 g (0.056 mol, 0.55 eq)

Ca(OH)$_2$ is charged into the flask, then heated up to 45~50° C. and stirred at this temperature for 0.5 h. A hot filtration used to remove some inorganic insoluable impurities gives 124.0 g of filtrate. Excess of NH$_3$ in the filtrate is removed by distillation under vacuum and the resulting residue is diluted by adding fresh ethanol. Then the solution is heated to 60~70° C. and 24.1 g (0.244 mol, 2.4 eq) conc. HCl aq. is added drop wise into the flask to give a suspension. The suspension is stirred at 60~70° C. for 0.5 h, then cooled down to 0~5° C. slowly and allowed to stir for an additional hour. The suspension is filtered and washed with ethanol two times to obtain 29.0 g wet product as solid, which is dried at 55° C. using vacuum for 8 h to obtain 18.3 g product as solid (86.2% in yield with 99.77% HPLC-purity).

Mass spectrum (ESI$^+$): m+1−2HCl/z=136

Example 3

Step A Pinner Reaction 98 mL (6.8 v/w of 4-ABN) methanol and 14.4 g (0.122 mol, 1.0 eq) 4-ABN are charged into a 250 mL flask under N$_2$ to obtain a solution. The mixture is cooled to −10° C., 44.5 g (1.22 mol, 10.0 eq) HCl gas is bubbled into the reaction solution (dried through conc. H$_2$SO$_4$) while keeping the temperature below 20° C. After bubbling the HCl gas, the reaction mixture is heated up to reflux for 10 h, cooled to room temperature and allowed to stir for an additional hour.

The suspension is then filtered to obtain 28.0 g of wet product as solid.

Mass spectrum (ESI$^+$): m+1−2HCl/z=151;
$^1$H NMR: $\delta_H$ 4.17-4.19 (3H, s, 6-C); 6.70-6.74 (2H, d, 3-C); 7.88-7.92 (2H, d, 2-C).
$^{13}$C NMR: $\delta_C$ 58.9 (6-C); 113.3 (1-C); 122.6 (3-C); 128.9 (2-C); 131.4 (4-C); 166.9 (5-C).

Step B and C: are the same as in example 2.

Example 4

Step A Pinner Reaction 32.5 mL (2.5 v/w of 4-ABN) MeOH and 13.0 g (0.110 mol, 1.0 eq) 4-ABN are charged into a 250 mL flask, stirred to obtain a solution. Then 60.8 g (27.4% v/w, 0.456 mol, 4.15 eq) HCl in MeOH solution are added drop wise into the flask while maintaining the temperature below 20° C. The mixture is cooled to −10° C., 23.5 g (0.644 mol, 5.85 eq) HCl gas is bubbled into the reaction solution (dried through conc. H$_2$SO$_4$) while keeping the temperature below 20° C. The reaction mixture is heated up to 35~40° C. and allowed to stir for 17 h and cooled down to room temperature. After stirring for an additional 1 h, the suspension is filtered and washed with methanol to give 23.9 g of wet product as solid with 94.7% HPLC purity. The wet product is used for the next step without further treatment.

Mass spectrum (ESI$^+$): m+1−2HCl/z=151;
$^1$H NMR: $\delta_H$ 4.17-4.19 (3H, s, 6-C); 6.70-6.74 (2H, d, 3-C); 7.88-7.92 (2H, d, 2-C).
$^{13}$C NMR: $\delta_C$ 58.9 (6-C); 113.3 (1-C); 122.6 (3-C); 128.9 (2-C); 131.4 (4-C); 166.9 (5-C).

Step B and C Amination 39 mL (3 v/w of 4-ABN) ethanol and 23.9 g wet intermediate (C$_9$H$_{12}$N$_2$O.2HCl, from 0.110 mol 4-ABN) are charged into a 250 mL flask under N$_2$ at rt. 83.6 g (11.2% in ethanol, 0.551 mol, 5.0 eq) ammonia ethanol solution is added drop wise into the flask while keeping the temperature below 35° C. After addition, the reaction mixture is heated up to 35~40° C. for 2 h. 4.5 g (0.061 mol, 0.55 eq) Ca(OH)$_2$ is charged into the flask, then heated up to 45~50° C. and stirred at this temperature for 0.5 h. The suspension is hot filtered to remove some inorganic insoluble impurities to obtained 139.0 g of filtrate. Excess NH$_3$ in the filtrate is removed by distillation using vacuum, the resulting residue is diluted by adding fresh ethanol. Then this solution is heated to 60~70° C. and 19.6 g (0.199 mol, 2.4 eq) conc. HCl aq. is added drop wise into the flask to give a suspension, which is allowed to stir for 30 minutes and then cooled to 0~5° C. slowly. After additional stirring at 0~5° C. for 1 h, the suspension is filtered and washed with ethanol twice to give 22.1 g wet product as solid. After drying at 55° C. under vacuum for 8 h, 19.3 g product as solid (Overall yield 84.3% with 99.66% HPLC) is isolated.

Mass spectrum (ESI$^+$): m+1−2HCl/z=136

Example 5

Step A Pinner Reaction 47.0 mL (2 v/w of 4-ABN) MeOH and 23.6 g (0.200 mol, 1.0 eq) 4-ABN are charged into a 250 mL flask, stirred to obtain a solution. Then 26.0 g (30%, 0.22 mol, 1.1 eq) HCl in MeOH solution is added drop wise into the flask while keeping the temperature below to 30° C.

The resulting mixture is cooled to 5° C., 43.3 g (1.18 mol, 5.9 eq) HCl gas is bubbled into the reaction solution (dried through conc. H$_2$SO$_4$) while maintaining the temperature below 30° C. The reaction mixture is transferred into a pressure tube equipped with pressure gauge. (The total amount of methanol is 80 mL, 3.4 v/w of 4-ABN). The pressure tube is then sealed and heated to 35~40° C. for 5 h, where a maximum pressure of 3 atm is reached.

After cooling to room temperature and stirring for an additional 1 h, the pressure is released. The suspension is filtered and rinsed by methanol twice to obtain 48.0 g of wet product as solid, which is dried under vacuum at 50° C. for 8 h. 42.0 g product as solid is isolated (yield 94% with 94.7% HPLC purity).

Mass spectrum (ESI$^+$): m+1−2HCl/z=151;
$^1$H NMR: $\delta_H$ 4.17-4.19 (3H, s, 6-C); 6.70-6.74 (2H, d, 3-C); 7.88-7.92 (2H, d, 2-C).
$^{13}$C NMR: $\delta_C$ 58.9 (6-C); 113.3 (1-C); 122.6 (3-C); 128.9 (2-C); 131.4 (4-C); 166.9 (5-C).

Step B and C: Amination 18 mL (3 v/w of 4-ABN) methanol and 10.5 g wet intermediate (C$_9$H$_{12}$N$_2$O.2HCl, from 0.050 mol 4-ABN) are charged into a 250 mL flask under N$_2$ at rt. 31.0 g (11.0% in methanol, 0.200 mol, 4.0 eq) ammonia in methanolic solution is added drop wise into the flask while maintaining the temperature below 35° C. After complete addition the mixture is heated up to 35~40° C. for 2 h. 2.05 g (0.028 mol, 0.55 eq) Ca(OH)$_2$ is then charged into the flask, heated to 45~50° C. and stirred at this temperature for 0.5 h followed by hot filtration to remove some inorganic insoluble impurities to give 65.0 g filtrate. Excess NH$_3$ in the filtrate is removed by distillation using vacuum and the resulting residue is diluted by adding fresh methanol. The solution is heated to reflux and 7.4 g (0.075 mol, 1.5 eq) conc. HCl is added drop wise into the flask to give a suspension. Stirring is continued for 0.5 h at 60~70° C., then slowly cooled down to 0~5° C. and stirring continued for 1 h. The suspension is then filtered and washed with methanol twice to give 11.2 g wet product as solid, which is dried at 55° C. using vacuum for 10 h to obtain 8.84 g product as solid (yield 84.9% with 99.7% HPLC-purity).

Mass spectrum (ESI$^+$): m+1−2HCl/z=136

Example 6

Step B and C Amination 18 mL (3 v/w of 4-ABN) methanol and 10.5 g wet intermediate (C₉H₁₂N₂O.2HCl, from 0.050 mol 4-ABN) are charged into a 250 mL flask under N₂ at rt. 31.0 g (11.0% in methanol, 0.200 mol, 4.0 eq) ammonia in methanol solution is added drop wise into the flask while maintaining the temperature below 35° C. After charging of ammonia, the reaction mixture is heated to 35~40° C. for 2 h, then the mixture is cooled to rt slowly and stirred for an additional 1 h. The reaction mixture is filtered to remove inorganic salts and rinsed with 10 mL methanol to obtain 65.0 g of filtrate. Excess NH₃ in the filtrate is removed by distillation using vacuum, the resulting residue is diluted by adding fresh methanol. The mixture is heated to reflux and 7.4 g (0.075 mol, 1.5 eq) conc. HCl is added drop wise into the flask to give a suspension. Stirred at 60~70° C. is continued for 0.5 h and the mixture subsequently cooled down to 0~5° C. and stirred for an additional 1 h at 0~5° C. The suspension is filtered and washed with methanol twice to give 13.0 g wet product as solid, which is dried at 55° C. using vacuum for 10 h to give 9.2 g product as solid (88.4% in yield with 99.8% HPLC purity).

Mass spectrum (ESI⁺): m+1−2HCl/z=136

Example 7

Step B and C, Amination 253 mL (3 v/w of 4-ABN) methanol and 184.0 g wet intermediate (C₉H₁₂N₂O.2HCl, from 0.715 mol 4-ABN) are charged into a 2 L flask at rt. 486.0 g (10.0% in methanol, 2.86 mol, 4.0 eq) ammonia in methanol solution is added drop wise into the flask while keeping the temperature below 35° C. After addition of ammonia the reaction mixture is heated to 35~40° C. for 2 h, then the mixture is cooled down to rt and stirred for an additional 1 h. The reaction mixture is filtered and rinsed with 85 mL methanol to obtain 1.0 L of filtrate. Excess NH₃ in the filtrate is removed by distillation using vacuum, the resulting residue is diluted by adding fresh methanol. The reaction mixture is heated to reflux to obtain a solution and 106.0 g (1.07 mol, 1.5 eq) conc. HCl aq. is added drop wise into the flask under reflux. The mixture is stirred at 60~70° C. for 0.5 h, cooled down to 0~5° C. slowly and allowed to stir at 0~5° C. for 1 h. The suspension is then filtered and washed with methanol twice to obtain 170.0 g wet product as solid, which is dried at 55° C. under vacuum for 11 h to obtain 132.0 g product as solid (88.7% yield with 99.3% HPLC purity).

Mass spectrum (ESI⁺): m+1−2HCl/z=136

Example 8

Step A Pinner Reaction 61.0 mL (5.2 v/w of 4-ABN) EtOH and 11.8 g (0.100 mol, 1.0 eq) 4-ABN are charged into a 250 mL flask to obtain a solution. The mixture is cooled down to 5° C., 44.0 g (1.2 mol, 12.0 eq) HCl gas is bubbled into the reaction solution (dried through conc. H₂SO₄) while maintaining the temperature below 20° C. The reaction mixture is transferred into a pressure tube equipped with pressure gauge, rinsed with 10 mL EtOH (The total amount of ethanol is 71 mL, 6.0 v/w of 4-ABN), sealed and heated to 35~40° C. for 5 h (maximum inner pressure is 3.4 atm. The mixture is then allowed to cool to rt, stirred 1 h, and the pressure released. The resulting suspension is filtered, and the filter cake rinsed with 12 mL ethanol two times to obtained 23.0 g of wet product as solid, which is used for the following step without further treatment.

Mass spectrum (ESI⁺): m/z=m+1−2HCl/z=165;

¹H NMR: δ_H 1.36-1.43 (3H, triple, 7-C); 4.51-4.57 (2H, tetra, 6-C); 6.76-6.80 (2H, d, 3-C); 7.90-7.99 (2H, d, 2-C).

¹³C NMR: δ_C 13.6 (7-C); 68.4 (6-C); 111.2 (1-C); 114.0 (3-C); 123.1 (2-C); 133.5 (4-C); 169.5 (5-C).

Compounds of general formula (I) are prepared analogously to the procedure described above.

We claim:
1. A process for the preparation of a compound of formula (I),

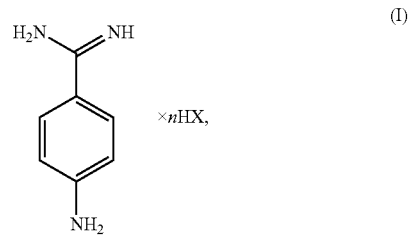

wherein n is 1 or 2 and X is Cl or Br, wherein the process comprises reaction step (B):
(B) treating compound (II) with an alcoholic solution of ammonia,

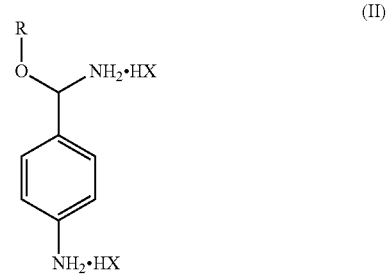

wherein R is methyl, ethyl, propyl, or butyl, and X is Cl or Br.

2. The process for the preparation of a compound of formula (I) according to claim 1, wherein the process comprising reaction steps (A) and (B):
treating 4-aminobenzonitril (III) with HX in a pure or mixed alcoholic solvent at a reaction pressure of about 0 to 10 atm

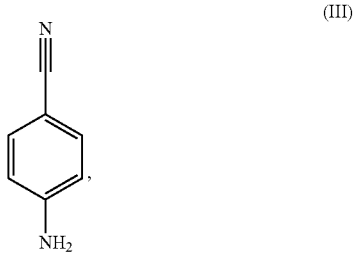

to form compound (II)

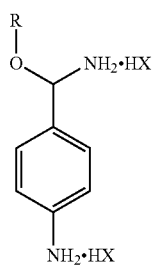

wherein if R is ethyl, the reaction pressure is between 2 to 6 atm.

3. A process for the preparation of a compound of formula (I),

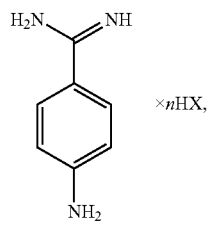

wherein n is 1 or 2, and X is Cl or Br, wherein the process comprises reaction steps (A), (B), and (C):

treating 4-aminobenzonitril (III) with HX in a pure or mixed alcoholic solvent at a reaction pressure of about 0 to 10 atm

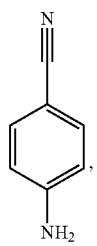

to form compound (II)

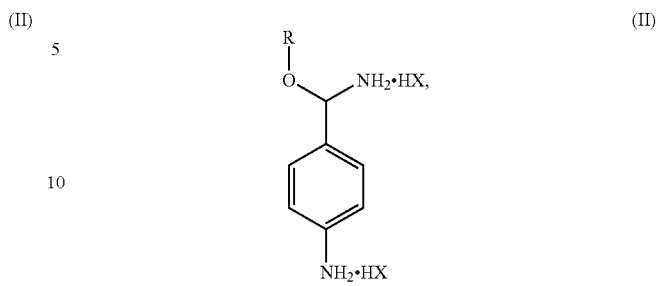

wherein if R is ethyl, the reaction pressure is between 2 to 6 atm;

treating compound (II) with an alcoholic solution of ammonia, wherein R is methyl, ethyl, propyl, or butyl, and X is Cl or Br; and (C) precipitating compound (I) by acidification with aqueous HX, wherein the steps (A), (B) and (C) take place successively in the order specified.

4. The process for the preparation of a compound of formula (I) according to one of claims 1 to 3, wherein the alcoholic solvent or alcoholic solution is ethanolic or methanolic.

5. The process for the preparation of a compound of formula (I) according to one of claims 1 to 3, wherein the alcoholic solvent or alcoholic solution is methanolic.

6. The process according to claim 3, wherein the alcoholic solvent or alcoholic solution in steps (A), (B), is the same and is ethanolic or methanolic.

7. The process according to one of claims 1 to 3, wherein the HCl or HBr in step (A) or step (B) is in a concentration from 5% to 30% (weight %) in alcohol.

8. The process according to one of claims 2 to 3, wherein a molar ratio of HCl or HBr to compound (III) is from 2:1 to 20:1.

9. The process according to one of claims 2 to 3 wherein the reaction according to step (A) is conducted at a temperature from −10° C. to 80° C.

10. The process according to one of claims 1 to 3, wherein the step (B) is run at the temperature from 20° C. to 80° C.

11. The process according to one of claims 1 to 3, wherein the reaction is run in $NH_3$ in an alcohol solution with a concentration of $NH_3$ from 5% to 30% (weight %).

12. The process according to one of claims 1 to 3, wherein the molar ratio of $NH_3$ to compound (II) is from 2:1 to 20:1.

\* \* \* \* \*